United States Patent [19]

Lim

[11] Patent Number: 5,433,694

[45] Date of Patent: Jul. 18, 1995

[54] PENILE ELEVATOR

[76] Inventor: Seung-Hyun Lim, 1-406, Geukdong Apartment, Oksu-dong, Sungdong-gu, Seoul, Rep. of Korea

[21] Appl. No.: 227,467

[22] Filed: Apr. 14, 1994

[30] Foreign Application Priority Data

Sep. 28, 1993 [KR] Rep. of Korea ............ 1993-20170

[51] Int. Cl.⁶ ................................................ A61F 2/26
[52] U.S. Cl. ..................................................... 600/38
[58] Field of Search .................................. 600/38–41; 623/11; 128/DIG. 25

[56] References Cited

U.S. PATENT DOCUMENTS

| 3,920,007 | 11/1975 | Line ............................ 600/39 |
| 4,151,841 | 5/1979 | Barrington . |
| 4,267,829 | 5/1981 | Burton et al. . |
| 4,335,714 | 6/1982 | Edgerton et al. ............ 600/40 |
| 4,411,260 | 10/1983 | Koss ............................ 623/11 X |
| 4,602,625 | 7/1986 | Yachia et al. ............... 600/40 |
| 4,807,608 | 2/1989 | Levius . |
| 4,988,357 | 1/1991 | Koss ........................... 600/40 X |
| 5,129,880 | 7/1992 | Grundei . |

FOREIGN PATENT DOCUMENTS

| 0782809 | 11/1980 | U.S.S.R. ....................... 600/39 |
| 8500513 | 2/1985 | WIPO .......................... 600/39 |

OTHER PUBLICATIONS

Jonas et al, "Silicone-Silver Penile Prosthesis: Description, Operative Approach and Results", Jun. 1980, 865–867.

Primary Examiner—Lee S. Cohen
Assistant Examiner—Samuel Gilbert
Attorney, Agent, or Firm—Richard C. Woodbridge

[57] ABSTRACT

The present invention relates to a penile elevator for treatment of a patient suffering from erectile impotence, when the penile elevator according to the present invention is surgically implanted under the skin of the lower abdomen and the penis, the patient suffering from the erectile impotence may easily perform the act of sexual intercourse, and more particularly, the penile elevator according to the present invention can easily slide according to the expansion or shrinkage of the penis to thereby be expanded or shrunk, and at the same time, the same is bendable to thereby render a patient no problem in his everyday life.

7 Claims, 3 Drawing Sheets

FIG.1A
FIG.1B
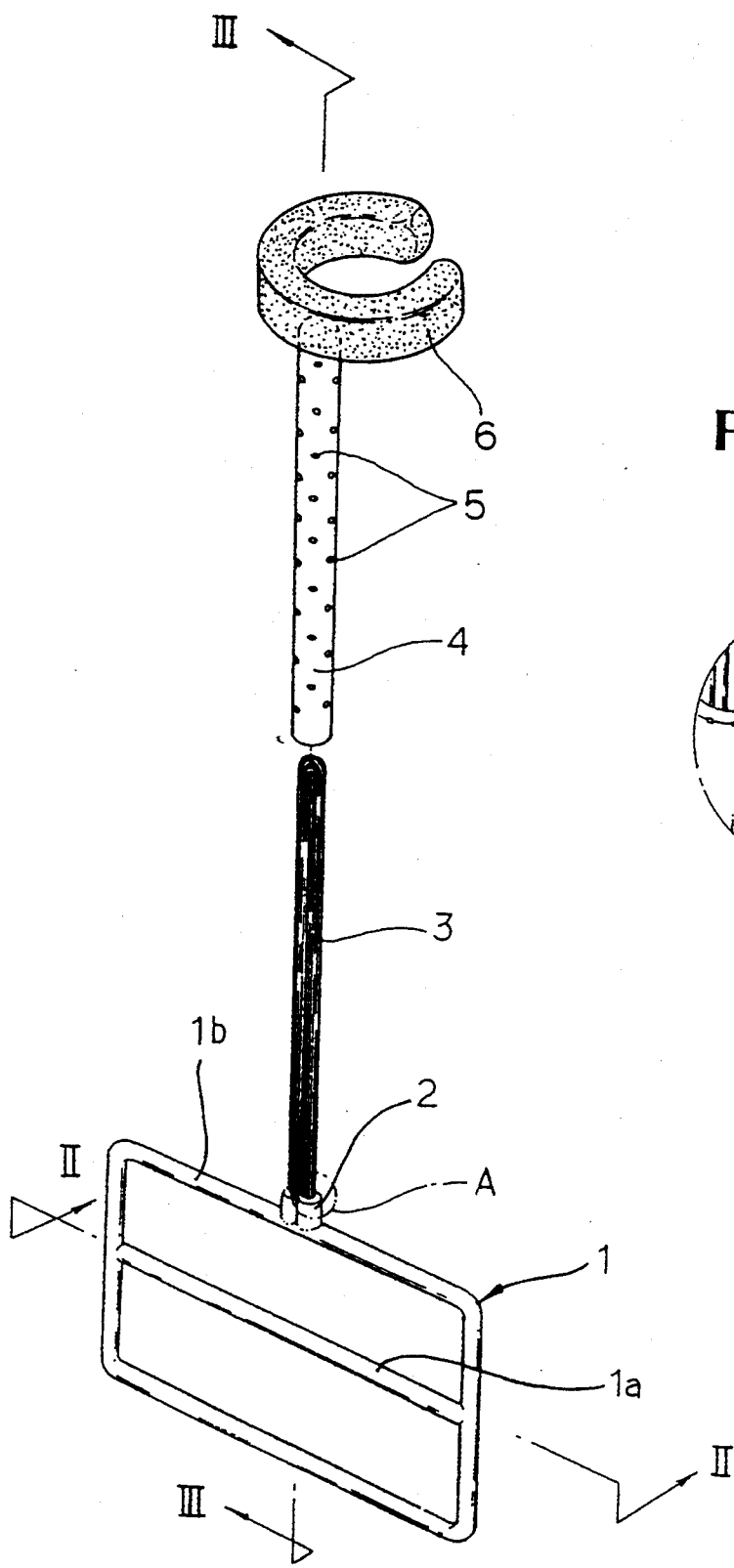
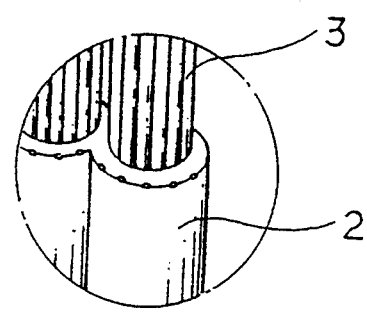

FIG.3
FIG.4
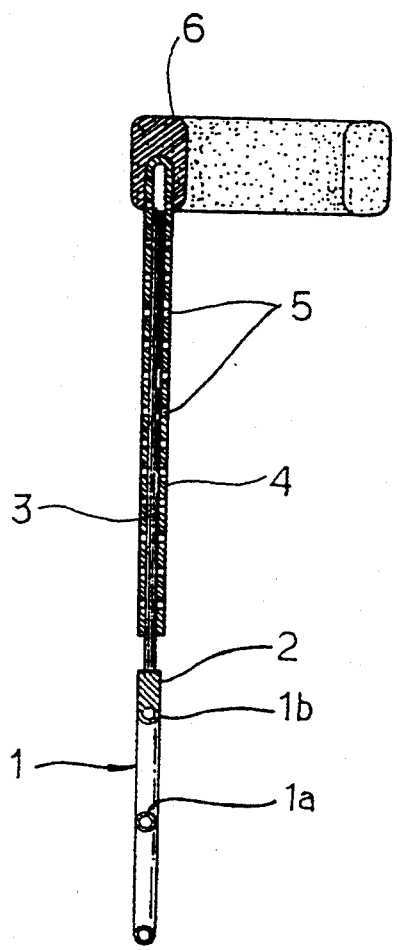
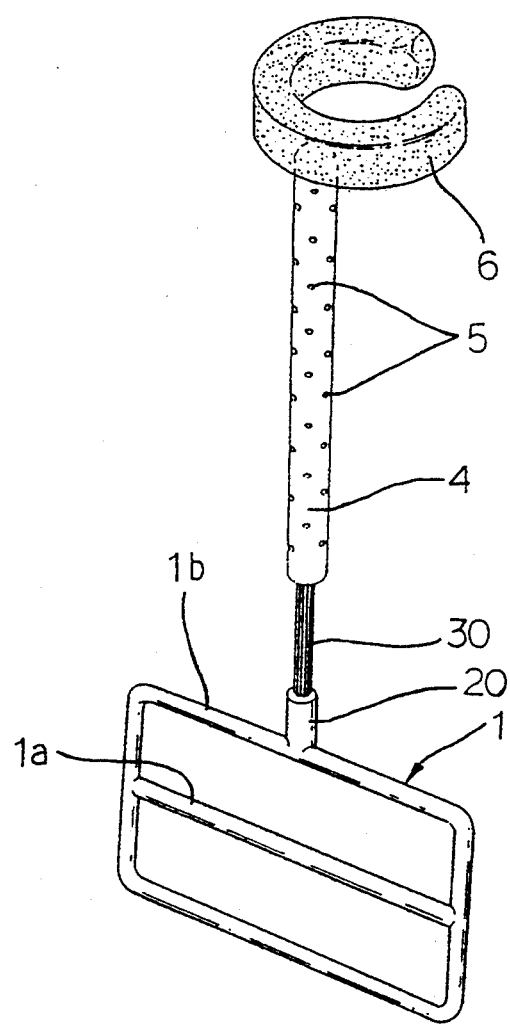

PENILE ELEVATOR

BACKGROUND OF THE INVENTION

1. Field of the Invention

The present invention relates to a penile elevator for treatment of a patient of erectile impotence which is a relatively frequent occurrence, The penile elevator according to the present invention implies a device which can be implanted under the skin of the lower abdomen and the scrotum by an operational method to thereby allow the patient of erectile impotence to engage in successful copulation at will, and the penile elevator according to the present invention is constructed to allow a cylinder member to elongate or shrink against a support member according to the erection or shrinkage of the penis.

2. Description of Prior Art

The use of implantable, inflatable penile prosthesis for the management of erectile impotence is described in U.S. Pat. Nos. 4,151,841, 4,267,829, 4,807,608, 5,129,880 and the like.

According to the penile prosthesis described in these U.S. Patents, in order to implant the prosthesis in the scrotum of the patient, a method of surgical treatment has been adopted wherein spongy tissue comprising the scrotum is cut open by a surgical knife and thereafter a flexible or expansible penile prosthesis is fixedly implanted.

The treatment method of erectile impotence by way of fixedly implanting the conventional penile prosthesis in the spongy tissue of the penis has a drawback in that the spongy tissue which is the inner structure of the penis should be destructed and the penile prosthesis should be fixedly implanted therein, which calls for complex surgical processes, and in the case of psychogenic or neurogenic erectile impotence, or physically curable erectile impotence as causes of the impotence, if the causes therefor are discovered and are thereby recovered, there is no way of reinstating the spongy tissue to its former condition because the tissue has been completely damaged even though the prosthesis fixedly implanted in the spongy tissue of the penis is removed, thus causing a user to be a permanent patient of erectile impotence.

Furthermore, there is another drawback in that the user is awkwardly limited in his social activities because the penile prosthesis fixedly implanted in the spongy tissue of the penis is always placed in an upright position.

SUMMARY OF THE INVENTION

Accordingly, the present invention is disclosed to solve the aforementioned problems and it is an object of the present invention to provide a penile elevator for being surgically and fixedly implanted under the skin of the penis and the lower abdomen, so that a patient of erectile impotence can be safely and simply cured thereof for engagement in successful copulation.

It is another object of the present invention to provide a penile elevator which can be easily removed by a surgical method from under the skin of the penis and the lower abdomen in case the erectile impotence resulting from psychogenic or physical causes are cured.

It is a further object of the present invention to provide a penile elevator which can be elongated or shrunk according to elongation or shrinkage of the penile erection.

It is a still further object of the present invention to provide a penile elevator which can be easily bent and stretched due to its fixed placement under the skin of the penis and the lower abdomen.

The penile elevator according to the present invention comprises: a pad made of a stainless steel with a small diameter and coated by medically acceptable silicone on a peripheral surface thereof; a fixing means for one end of which being fixed to an external supporter of the pad and for the other end thereof being opened; a support means for being inserted into the opening of the fixing means and for being composed of a plurality of silvery strands fixed by mechanical force; a cylinder member for being inserted into a peripheral surface of the support means according to expansion or shrinkage of the penis, so that the cylinder member can be shrunk or elongated; and a silicone ring for being disposed at a tip of the cylinder member and for wrapping a peripheral surface of the penis crosswise under the skin of the lower glans.

BRIEF DESCRIPTION OF THE DRAWINGS

Other objects and aspects of the invention will become apparent from the following description of embodiments with reference to accompanying drawings in which:

FIG. 1A is a perspective view of one embodiment according to the present invention;

FIG. 1B is an enlarged sectional view of "A" part in FIG. 1A wherefrom a silicon film layer and an coated layer are removed to thereby be enlarged for illustration;

FIG. 3 is a sectional view drawn along III—III line in FIG. 1A; and

FIG. 4 is a perspective view of a penile elevator according to another embodiment of the present invention.

DETAILED DESCRIPTION OF THE INVENTION

Figure 2A:
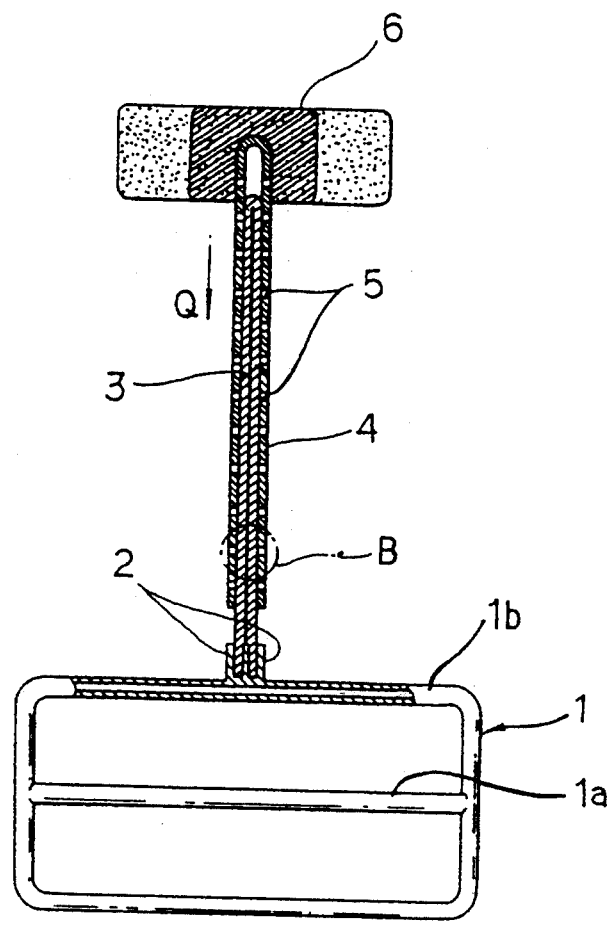
FIG. 2A is a sectional view drawn along II—II line in FIG. 1A.

As described in FIGS. 1, 2 and 3, the penile elevator according to the present invention comprises: a stainless steel pad 1 for being fixed by a surgical method under the skin of the lower abdomen; a support means 3 for being fixedly inserted at one end thereof to a fixing member 2 of the pad 1; a cylinder member 4 for being slidingly wedged into a peripheral surface of the support means 3 to thereby be shrunk or elongated according to the erection of shrinkage of the penis; and a silicone ring 6 for being fixed on a tip of the cylinder member 4 to thereby wrap the penis under the skin of the lower glans.

In the above description, the pad 1 has a rectangular shape made of stainless steel pipe with a small diameter. The pad 1 is fixedly welded at both ends of a support 1a in order to prevent twist and the like at the center thereof.

There is disposed a pair of fixing members 2 for fixing the support means 3 by mechanical force whereby one end of the support means 3 is inserted into a center of an external support 1b against the support 1a.

An external surface of the pad 1 is coated by medically acceptable silicone. The fixing members 2 is made of stainless steel pipe same kind as that off the pad 1, and the fixing members 2 has an opening, into which a tip (a lower side of the support means 3 at FIGS. 1A and 2A) of the support means 3 comprising a plurality of thin silvery strands is inserted.

The peripheral surface of the fixing member 2 is pressed mechanically, so that the support means 3 is fixed to the fixing means 2.

Figure 2B:
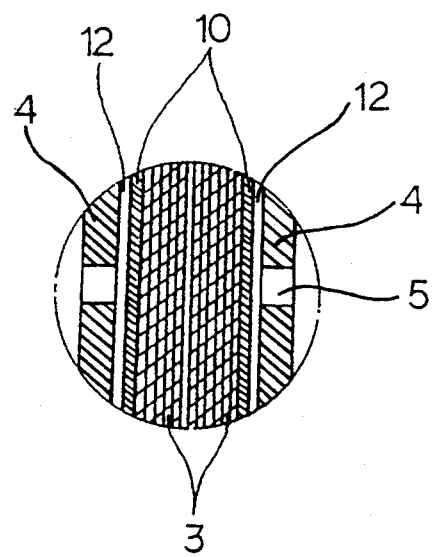
FIG. 2B is an enlarged sectional view for illustrating "B" part of FIG. 2A in an enlargement.

Meanwhile, the support means 3 comprising a plurality of silvery strands, as illustrated in detail at FIGS. 1B and 2B, is wrapped by coated layer 10 made of "Teflon" (PFA), polyethylene, artificial rubber and the like, and a peripheral surface thereof is coated by a silicone film layer 12 comprising medically acceptable silicone and the like.

The cylinder member 4 is receptible to the support means 3 and at the same time, is formed with a hollow lengthwise in order for the same to slide against the support means 3 according to the erection or shrinkage of the penis.

The hollow of the cylinder member 4 can be formed in a round, oval or other shape in a cross-sectional view if cut vertically against the length of the penis but the oval shape is ostensibly desirable when a surgical operation is performed.

Furtheremore, it is recommendable that the length of the cylinder member 4 should be the same as that of the support means 3 or shorter than that of the support means 3.

When the penile elevator according to the present invention is surgically implanted under the skin of the penis, the cylinder member 4 helps the bodily fluid circulate freely and is formed with a plurality of holes 5 to thereby prevent the patient from being inflamed.

A tip of the cylinder member 4 is fixed by an adhesive means (not shown) to a silicone ring 6 which has an opening at one end thereof.

The cylinder member 4 and the silicone ring 6 can be extruded for an integral formation. It is advisable that the silicone member 4 and the silicone ring 6 should have hardness of 1–80 degree but it is preferred that the hardness of the silicone ring 6 should be less than that of silicone member 4.

The silicone ring 6 is disposed under the skin of the penis glans to thereby wrap longitudinally a peripheral surface of the penis. One side of the silicone ring 6 is purposely opened so that the penis can easily elongate or shrink longitudinally according to the expansion or shrinkage of the penis.

FIG. 4 is a perspective view of a penile elevator according to another embodiment of the present invention.

The difference between the penile elevator illustrated in FIG. 4 and the embodiment according to the present invention illustrated in FIGS. 1, 2 and 3 is that the penile elevator in FIG. 4 has one fixing means 20 at an external support 1b of the pad 1 and the fixing means 20 is inserted by one rod of support means 30 at one end thereof comprising thin silvery strands and mechanically pressed, and then the fixing means 20 is fixed to the support means 30.

The operation and effect thereof with regard to the embodiment thus constructed according to the present invention will now be described.

First of all, a stainless steelpipe is cut and welded to produce a pad 1 comprising the external support 1b and the middle support 1a as illustrated in FIG. 1A. A pair of fixing means 2 is fixedly welded near a central area of the external support 1b. External surfaces of the pad 1 and the fixing means 2 are coated by medically acceptable silicone, so that the surface is agreeable to the touch.

Tip ends of two-rod support means 3 are respectively inserted into the opening of a pair of fixing means 2 fixed to the pad 1, mechanically pressed, and then the tip ends of the support means 3 are firmly fixed to the fixing means 2.

At this time, because the peripheral surface of the support means 3 is wrapped by a coated layer 10 of Teflon and the like, the layer 10 and an inner periphery of the fixing means 2 are firmly and tightly secured.

As seen in the aforesaid description, the support means 3 is composed of thin silvery strands which are wrapped by the layer 10 of Teflon at the periphery thereof.

The support means 3 is now folded at the center thereof and two ends of the support means 3 can be in turn inserted into the opening of the fixing means 2.

Now, the external surfaces of the support means 3 and fixing means 2 are wrapped by the medically acceptable silicone to thereby form a silicone-film layer 12 and the support means 3 is inserted through the opening side (more precisely through the lowest end side thereof) of the cylinder member 4 attached with the silicone ring 6 at the tip end thereof.

As seen from the foregoing, the pad 1 of the penile elevator according to the present invention wherein the support means 3 is slidingly inserted into the hollow of the cylinder member 4 is surgically implanted under the skin of the lower abdomen and the penis of the patient suffering from erectible impotence, and the silicone ring 6 secured at the tip end of the cylinder member 4 and wrapped around the support means 3 is securely implanted under the skin of the penis.

As described above, under a condition the penile elevator according to the present invention is securely implanted under the skin of the penis and the lower abdomen of the patient suffering from the erectile impotence, and when the penis is elongated (expanded) according to urge of sexual needs, the cylinder member 4 is slid and elongated in the opposite direction from an arrow Q in FIG. 2A against the support means 3 to thereby allow the patient to engage in copulation, and when the copulation is over, the cylinder member 4 is slid toward the arrow direction Q in FIG. 2A according to the shrinkage of the panis to thereby reduce the length of the penis.

At this time, because the cylinder member 4 is formed with a plurality of holes 5 through which the bodily fluid can pass, the cylinder member 4 is smoothly slid through the intermediary act of the fluid around the support means 3 during the sliding of the cylinder member 4.

Meanwhile, when the penile elevator according to the present invention is implanted in a patient suffering from absolute no erection or premature ejaculation, the penile elevator according to the present invention maintains its length to thereby allow the patient to perform sexual intercourse under nonerect condition, and after the intercourse, the support means 3 of the penile elevator can be bent at a predetermined position to thereby allow no inconvenience in everyday life.

In other words, when the penile elevator according to the present invention is surgically implanted, the penis implanted with the penile elevator can not only perform a conventional function, but can also be adjusted at will according to the patient's needs, causing no problems in the day-to-day life.

The above description has described about the external surface of the support means 3 comprising a plurality of thin silvery strands wrapped by a layer 10 coated by Teflon and the like, the present invention is not limited to its specific embodiments. By way of example, in order to improve firmness of the support means 3, it should be apparent that the plurality of thin silvery strands can be twisted to thereafter be wrapped by a layer coated by Teflon and the like, which is not departing from the spirit and scope of the invention and the illustration thereof.

Furthermore, the invention has been described about only one silicone ring 6 secured at the tip end of the cylinder member 4 as illustrated in FIGS.1 and 4, the present invention is not limited to this specific embodiment. By way of example, it should be apparent that more than one silicone ring (two or three silicone rings) may be secured near the tip end of the cylinder member 4.

It should also be apparent that the present invention may assume various shapes or styles according to a physical condition, symptom of the patient, and the present invention may selectively be manufactured to use according to the size or thickness of the penis.

In other words, because the support means 3 disposed in the penis is made of extremely flexible silvery strands and because the erected support means 3 implies that the penis is in an erect condition, the function of the penis can smoothly be performed and in other occasions than that, the support means 3 can be bent for usual activities in everyday life.

Specifically, according to the present invention, because the cylinder member 4 having the approximate same length as that of the support means 3 is mounted on the outside of the support means 3, the cylinder member 4 mounted with the silicone ring 6 slidingly moves up and down with the support means 3 inserted into, thereby preventing the cylinder member 4 from being separated from the support means 3,, and the fluid is smoothly circulated through the plurality of holes 5 formed on the cylinder member 4, thereby minimizing occurrence of inflammation.

As seen from the foregoing, the penile elevator according to the present invention allows to be easily and safely implanted by a surgical method under the skin of the lower abdomen and the penis of the patient suffering from erectile impotence, so that a conventional complicated surgery involving destruction of spongy tissue of the penis can be dispensed and no physical or mental burden is given to the patient.

Furthermore, the penis can be bent or erected according to the needs regardless of the place or the time, thereby allowing the patient to wage everyday life without any problems incurred.

The penile elevator according to the present invention may assume various shapes, styles, sizes or thickness according to the physical condition or symptom of the patient to thereby maximize the surgical effect.

Still furthermore, if the erectile impotence resulted from physical or mental cause is restored to a normal condition in accordance with changed environmental condition of the patient, continued home treatment or regular attendence of a hospital, the penile elevator implanted under the skin of the lower abdomen and the penis can easily be removed to thereby restore 100% the function of the penis.

Having described specific preferred embodiments of the invention with reference to the accompanying drawings, it is to be understood that the invention is not to be limited to those precise embodiments, and that various changes and modifications may be effected therein by one skilled in the art without departing from the scope or spirit of the invention as defined in the appended claims.

What is claimed:

1. A penile elevator for supporting a shaft and glans of a human penis comprising:
   a pad (1) made of a stainless steel having a predetermined diameter and coated by medically acceptable silicone on a peripheral surface thereof;
   a support means (3) for supporting the pad composed of a plurality of strands;
   fixing means (2) for attachment to said support means (3), wherein one end of said fixing means (2) is fixed to said pad (1) and another end of said fixing means includes an opening therein, so that said support means (3) can be inserted into the opening of said fixing means (2) and held there by mechanical force;
   a cylinder member means (4) for substantially surrounding said support means (3), so that the cylinder member means (4) can move longitudinally on the support means according to the expansion or shrinkage of the penis;
   a plurality of holes (5) formed in said cylinder member means (4) so that said cylinder member means (4) can freely slide with respect to said support means (3); and,
   a silicone ring means (4) located at a tip of said cylinder member means (4) for wrapping the peripheral surface of the penis crosswise under the skin of the lower glans.

2. A penile elevator as described in claim 1 wherein said support means (3) includes a peripheral surface which is wrapped by a layer (10) coated by polytetrafluoroethylene.

3. A penile elevator as defined in claim 1 wherein said support means (3) includes a peripheral surface which is wrapped by a layer (10) formed with a silicone-coated film.

4. A penile elevator as described in claim 1 wherein said silicone ring means (6) is open at one end thereof in order to expand or shrink according to the crosswise expansion or shrinkage of the penis.

5. A penile elevator as defined in claim 1, wherein said silicone ring means (6) is less hard than said cylinder means (4) which has a hardness in the range of 1–80 degrees.

6. A penile elevator as defined in claim 1, wherein the cylinder member means (4) is attached to said silicone ring means (6).

7. A penile elevator for supporting a shaft and glans of human penis comprising:
   a metal pad (1) coated by a medically acceptable silicone on a peripheral surface thereof;
   support means (3) for supporting the pad comprised of a plurality of strands of material;
   fixing means (2) for attachment at one end to said pad (1) and another end of which includes an opening therein for receiving said support means (3);
   a cylinder member means (4) for surrounding said support means (3) so that said cylinder member means (4) can slide with respect to said support means (3) according to the expansion or shrinkage of the penis; and,
   a silicone ring means (6) attached to said cylinder member means (4) for surrounding and supporting the penis under the skin of the lower glans.

* * * * *